US007727175B2

(12) United States Patent  
Voegele

(10) Patent No.: US 7,727,175 B2  
(45) Date of Patent: Jun. 1, 2010

(54) DISK BANDAGE DISPENSER

(75) Inventor: James W. Voegele, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 516 days.

(21) Appl. No.: 11/557,655

(22) Filed: Nov. 8, 2006

(65) Prior Publication Data

US 2008/0108926 A1    May 8, 2008

(51) Int. Cl.
*A61F 13/00*    (2006.01)
*B43K 5/14*    (2006.01)
*B43K 5/18*    (2006.01)

(52) U.S. Cl. ............... 602/79; 602/41; 41/132; 41/133; 41/148

(58) Field of Classification Search ............ 604/47, 604/520, 244, 246, 285, 286; 606/117, 213–214; 128/200.1, 200.21; 401/205, 132–135, 137, 401/139, 145, 148; 602/41–43, 52, 54, 57, 602/19; 424/443, 447, 449, 457
See application file for complete search history.

(56) References Cited

U.S. PATENT DOCUMENTS 3,486,504 A * 12/1969 Austin, Jr. ............... 604/289
4,927,283 A * 5/1990 Fitjer ........................ 401/132
5,928,611 A   7/1999 Leung
6,217,603 B1   4/2001 Clark et al.
6,455,064 B1   9/2002 Narang et al.
6,536,975 B1 * 3/2003 Tufts ........................ 401/134
6,916,133 B2 * 7/2005 Hoang et al. ............ 401/133
2003/0182802 A1 * 10/2003 Vega et al. ................ 30/50
2004/0190975 A1   9/2004 Goodman et al.
2005/0147457 A1 * 7/2005 Badejo et al. ........... 401/132

OTHER PUBLICATIONS

U.S. Appl. No. 09/430,177, filed Oct. 29, 1999, Narang et al.

* cited by examiner

*Primary Examiner*—Tatyana Zalukaeva
*Assistant Examiner*—Ophelia Hawthorne
(74) *Attorney, Agent, or Firm*—Frost Brown Todd LLC

(57) ABSTRACT

A surgical device for applying a bandage onto tissue is disclosed. The surgical device has an actuator and contains one or more releasable bandages and an adhesive. Actuation of the actuator releases the adhesive, saturates the bandage with the adhesive, and releases the bandage onto tissue. The actuator can be squeezed, moved linearly, or rotated to dispense the adhesive onto the bandage and release the saturated bandage. The adhesive can be stored in an ampoule, or a sealed chamber. Actuation of the surgical device breaks the ampoule and/or seal and releases the adhesive for use. In addition to the adhesive, additional fluids or additives can be mixed with the adhesive or stored in separate chambers of the ampoule or surgical device. These additives can include drugs, image enhancing agents, necrosing agents, sclerosing agents, and the like.

15 Claims, 7 Drawing Sheets

DISK BANDAGE DISPENSER

FIELD OF THE INVENTION

The present invention relates, in general, to surgical bandages and more specifically, to surgical devices that can saturate a bandage with an adhesive and place the saturated bandage onto tissue.

BACKGROUND OF THE INVENTION

Adhesives and sealants have been contemplated to supplement or replace suture and staple based applications for many years. Fluid adhesives offer the special challenges of controlling the fluid placement, preventing fluid migration or drips within the body, creating barriers to tissue regrowth, adhesion difficulties to moist tissue, adhesive strength, and blockage of adhesive dispensing orifices in the surgical device. These issues and others have limited the adoption of adhesives.

If adhesives are applied to a porous carrier or bandage pad, the adhesive is drawn into the bandage by wicking or absorption and provides adhesion control. The adhesive can be provided either before or after the bandage is placed onto tissue. Additionally, other additives or compounds such as adhesive initiators, drugs, marking materials, contrasting agents, gene therapies and the like can be incorporated into the adhesive or combined with the bandage. The combination of bandage and adhesive and compound make many additional surgical applications practical including buttressing, drug delivery, fixation and the like. The bandage and adhesive can be permanent or temporary, for external or internal application, and can be used for open surgery, hand assisted laparoscopic surgery, or endoscopic surgery.

Dispensing fluids or gels can ooze, be difficult to control and adhesives and additives can drip into unwanted places. Furthermore, once opened to air, moisture or to adhesion initiators such as base solutions, atmospheric moisture, saline and the like can limit the storage time of the device.

Consequently, a significant need exists for a bandage and adhesive combination that offers a long storage life, offers improved adhesive placement, strong adhesive bonds, reduces adhesive migration, can be used in internal and external surgeries, offers additional features such as drug therapies, image enhancements and the like, controls or reduces the likelihood of blocking the adhesive distribution from the surgical device, and can be used for cutaneous and/or percutaneous surgery.

BRIEF SUMMARY OF THE INVENTION

The invention overcomes the above-noted and other deficiencies of the prior art by providing a surgical device for applying a bandage to tissue. The surgical device comprises a frame, and an adhesive dispensably sealed within a chamber of the frame. A bandage is provided having at least one porous layer. The bandage is located at a proximal end of the frame and located adjacent to the adhesive dispensably sealed within the chamber. An actuation mechanism is located on the frame and is operably coupled to the adhesive and the bandage such that actuation of the actuation mechanism dispenses the adhesive to saturate the at least one porous layer of the bandage, and releases the saturated bandage from the surgical device onto tissue Alternately, there is provided an alternate surgical device for applying a bandage onto tissue. The alternate surgical device comprises a frame and an adhesive releasably sealed within a bore of the frame. One or more bandages are movably located within an open end of the bore. Each of the one or more bandages has a non-permeable barrier creating a seal with the bore, and at least one porous layer. The non-permeable barrier of a proximal most one of the one or more bandages releasably seals the adhesive within the bore. A rotary actuator is rotatably attached to the frame. Rotation of the rotary actuator moves the one or more bandages longitudinally to release the adhesive, to saturate a distal most one of the one or more bandages, and to apply the distal most one of the one or more bandages from the surgical device onto tissue.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
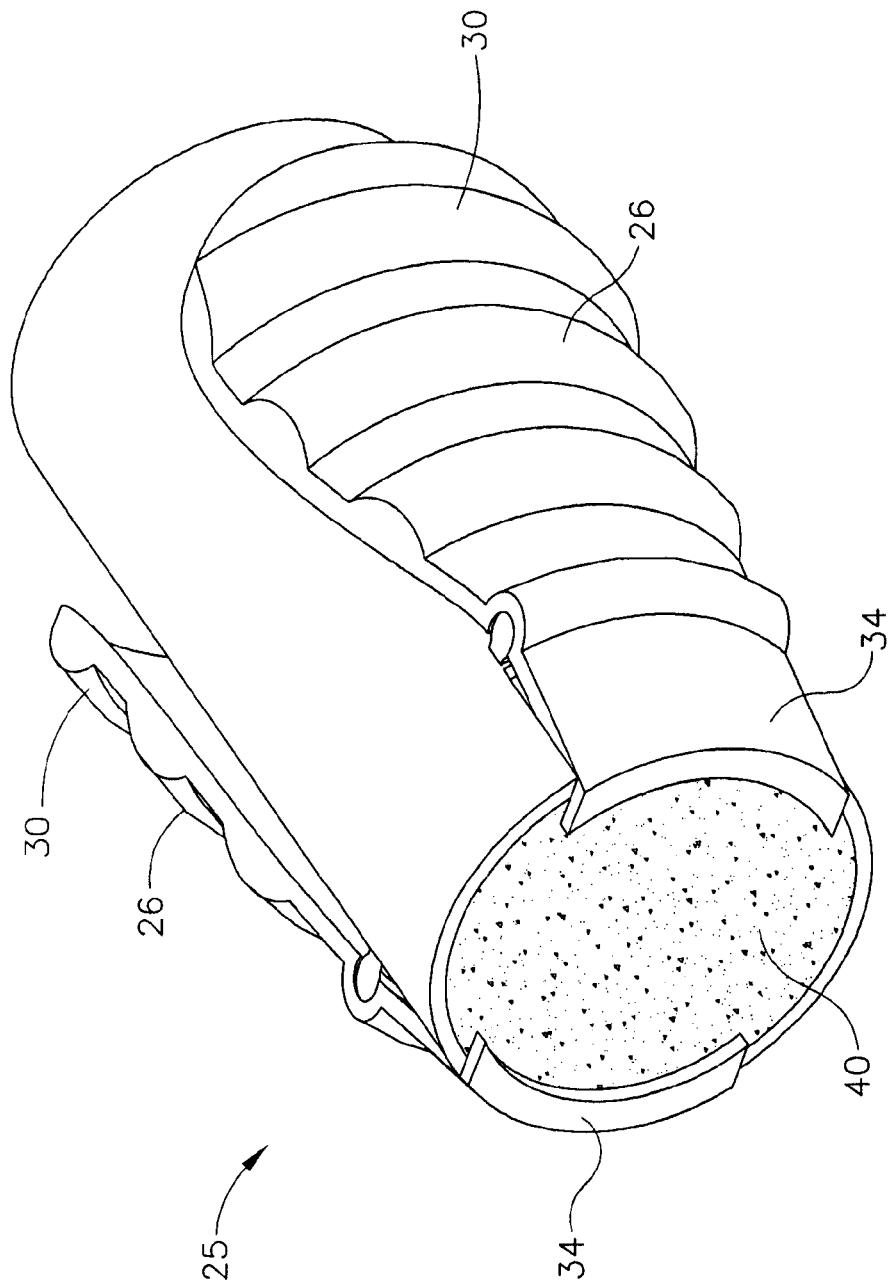
FIG. 1 is an isometric view of a squeeze activated surgical device that can adhere a porous disk bandage onto tissue.

Turning to the Figures, wherein like numerals denote like components throughout the several views, in FIG. 1 a surgical device 25 is shown that can be used to adhere a bandage onto tissue. The surgical device 25 contains a releasable fluid 50 such as an adhesive 51 and at least one disc shaped dispensable surgical bandages 40. The surgical device 25 of FIG. 1 has a grip 26 with one or more actuators 30 that can be actuated to apply adhesive 51 to saturate the surgical bandage 40, and to release the surgical bandage 40 to adhere onto tissue. Surgical bandages 40 can have many usages such as but not limited to one or more of: a tissue fastener to replace sutures and staples, a buttress used alone or in combination with suture and/or staples, a drug delivery device, a surgical marker, a sensor target, a hemostasis bandage to staunch the flow of blood, and the like. Surgical bandages 40 by way of example can be used both externally and internally, can be any size or shape, and fluid 50 or bandage 40 may be colored to make it readily observable by the naked eye.

Figure 2:
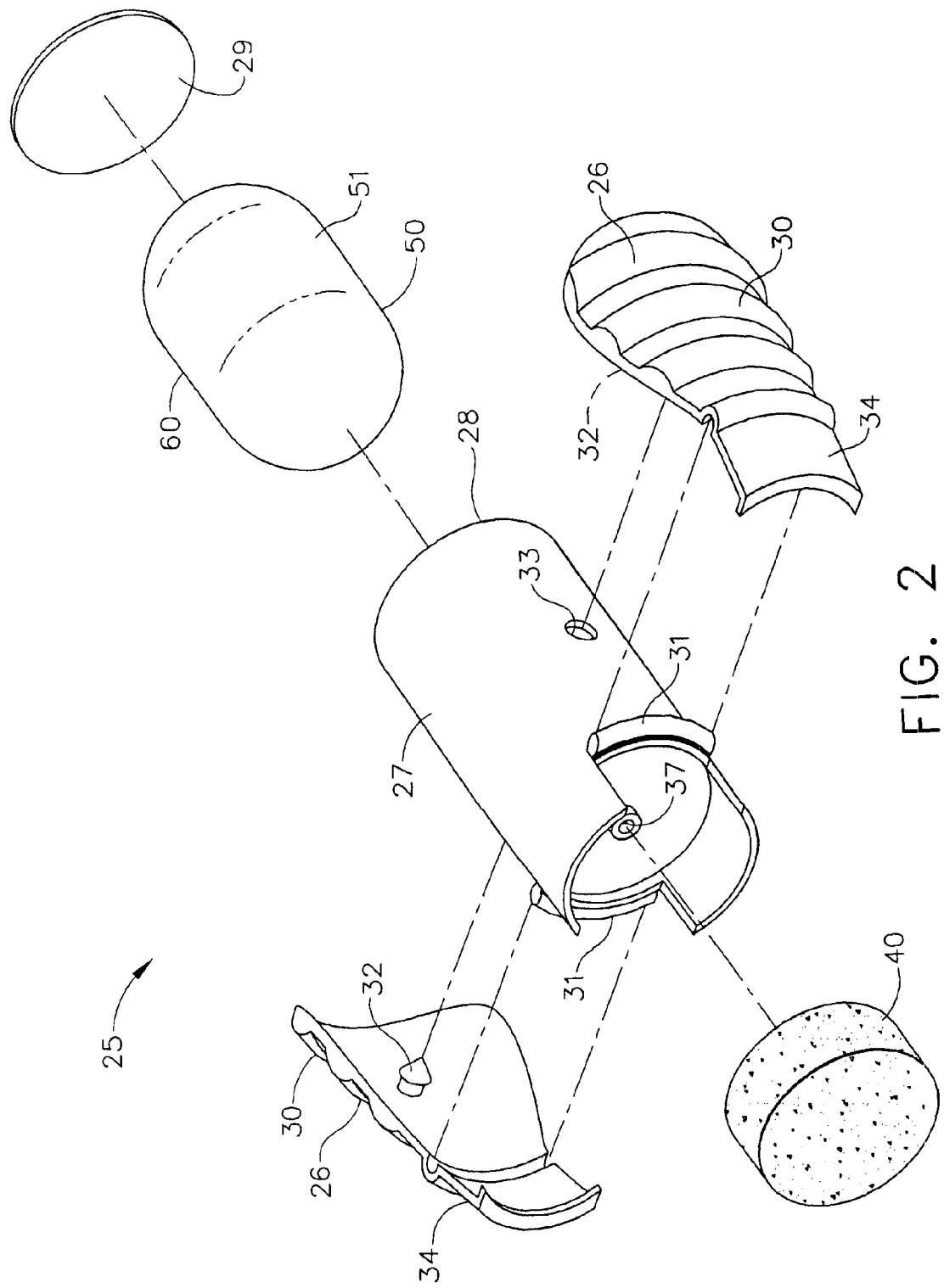
FIG. 2 is an exploded isometric view of the surgical device of FIG. 1.

The surgical device 25 shown in the exploded view of FIG. 2 comprises a deflectable frame 27 containing a frangible ampoule 60 with fluid 50 therein. The fluid 50 within the ampoule 35 is the adhesive 51 to adhere the surgical bandage 40 to tissue. Ampoule 60 is contained within a chamber 28 of frame 27 and ampoule 60 is sealed to prevent deterioration or degradation of the fluid 50 contained therein. Frame 27 by way of example is constructed of a squeezably deformable material such as polyethelelene, polypropelene, nylon, malleable materials such as aluminum, or any one of a number of suitable engineering materials. A plug 29 fixedly attaches to a distal end of chamber 28 and locks ampoule 60 therein. A pair of actuators 30 pivotally mount on ribs 31 on frame 27 with each actuator 30 having an ampoule stress concentrator 32 thereon. Actuators 30 are pivotally attached to frame 27 by snapping ampoule stress concentrators 32 within openings 33. The snapping action attaches actuators 30 to frame 27 and places stress concentrators 32 adjacent to frangible ampoule 60. Stress concentrators 32 for example, can be points, sharps, pins, blades, or any other device that can increase the load onto a small area to induce release expression of an adhesive or contents. A pair of bandage clamps 34 extend from actuators 30 into notches in frame 27 and hold bandage 40 therebetween.

Figure 3:
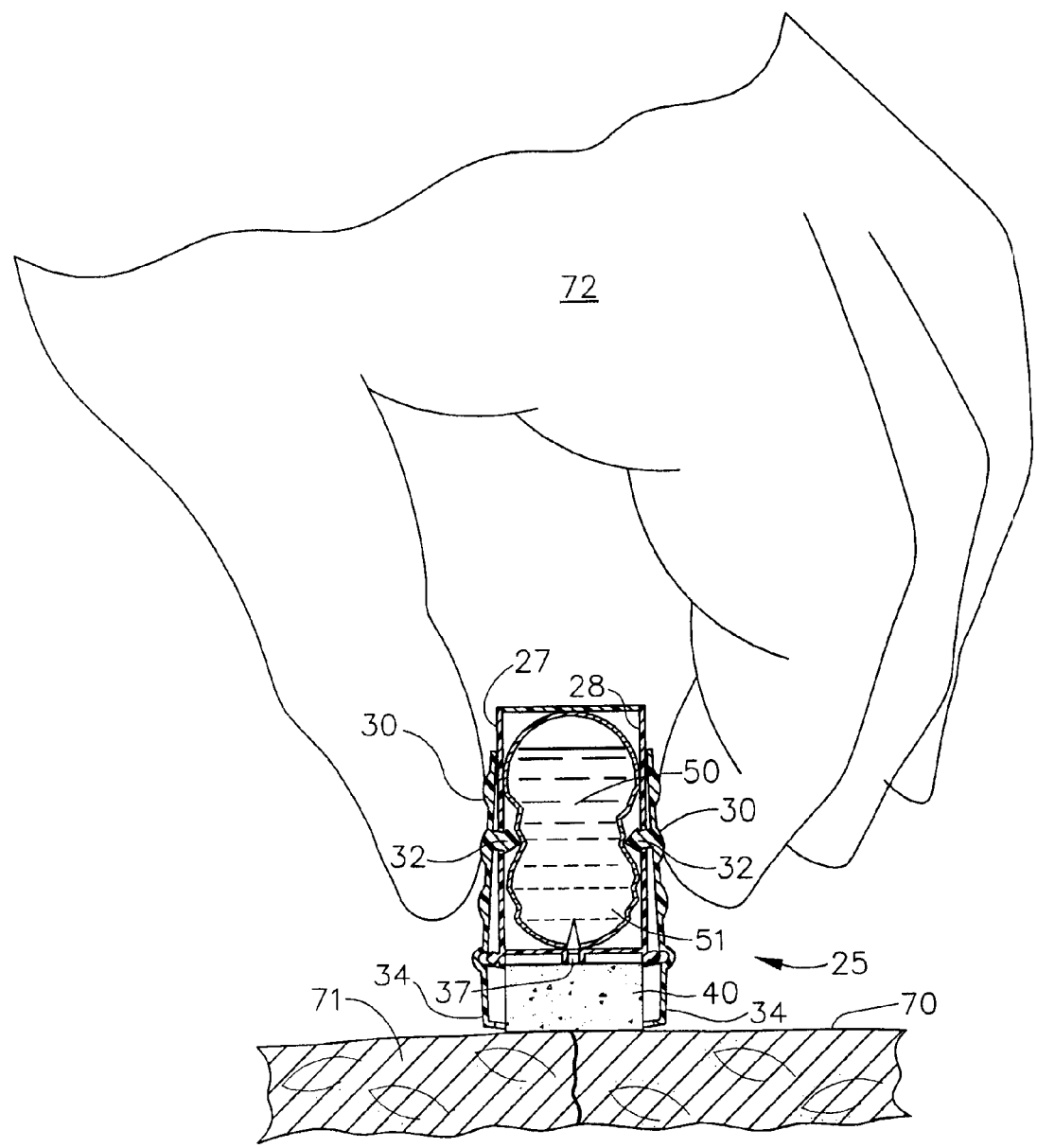
FIG. 3 is a cross sectional view of the surgical device of FIG. 1 with the porous disk bandage being placed on tissue as the surgeon squeezes a pair of actuators of the surgical device to release the adhesive, to saturate the bandage and to release the saturated bandage.

FIG. 3 shows a cross section of the surgical device 25 held in a surgeons hand 72 with bandage 50 placed into contact with tissue portions 70, 71. The surgeon is preparing to squeeze actuators 30 inwardly to bring stress concentrators 32 into contact with frangible ampoule 60 and break ampoule 60 releasing adhesive 51 from within. The squeezing action deflects the walls of the frame 27 as the ampoule 60 is breached. As the surgeon continues to squeeze the actuators 30, the adhesive 51 flows from chamber 28, into passage 37, and saturates bandage 40. Further squeezing spreads bandage clamps 34, releases bandage 40 saturated with adhesive 50 from the surgical device 25 onto tissue, and enables the surgeon to remove the surgical device 25 sans bandage 40.

The fluid 50 could be a single material neat, or a combination of materials. As used herein, the term "fluid" comprises liquids, gases, gels, microparticles, and any other material which can be made to flow between a pressure gradient. Fluids 50 may be any viscosity that can be moved by the surgical device. Additionally, fluid 50 may undergo a property or phase change within the patient from a fluid to a solid, or from a solid to a fluid or any state between fluid and solid. By way of example, the phase change could involve cross linking or polymerization or responses to temperature moisture or other trigger mechanisms.

Additionally, whereas one ampoule 60 is shown by example, the number of ampoules 60 can be one or more and each ampoule 60 can contain the same fluid 50, or different ampoules 60 could contain different fluids 50.

The Bandage:

The bandage 40 is biocompatible and may be one or more layers of a porous structure such as a gauze, an open cell foam, a mesh, or any other porous structure. Bandage 40 may be used internally or externally, can be implantable or non-implantable, and could be constructed from bioabsorbable or biodegradable materials such as polylactic acid, polyglycolic acid, polyglactin, polydioxanone, polyglyconate, whey protein, cellulose gum, starch, gelatin, and polydioxanone. Additionally, bandage 40 can be constructed from non-absorbable materials. These non-absorbable materials could be but are not limited to metallic materials such as stainless steel, titanium, and gold, and to non-metallic materials such as silk, cotton, nylon, polypropylene, braided polyester, polybutester, polyethylene, and polyetheretherketones (PEEK). Bandage 40 could be constructed as a dissolvable pellet, in layers, have non-permeable barrier layers, contain fluid absorbable or tamponade materials, have adhesive pre-applied thereto, or from any combination of absorbable or non-absorbable materials such as, by way of example, a cotton and polydioxanone mix. The durometer of bandage 40 may be of any durometer making it soft and pliable, to firm or hard for palpability or structure (scaffolding). Bandage 40 by way of example, may contain compounds such as but not limited to adhesives 51, additives 52 and/or adhesive initiators 53 listed below. For example, bandage 40 could contain both a detectable marker material such as barium, and an adhesive initiator 53. Additionally, by way of example, the bandage 40 can be used to superficially cover tissue areas, attain cellular attachment, become an implant, serve as a volume/bulking filler, increase in volume when dispensed with the fluid by having tamponade properties, or proximate two or more tissue or man-made components.

Ampoule

The ampoule 60 is a frangible sealed structure containing a fluid 50. When ampoules 60 are loaded by stress concentrators 32, they are breached or ruptured to release the fluid 50 within. Ampoules 60 can be sealed to provide stability, increase shelf-life, and prevent setting or polymerization of fluids 50 such as adhesive 51. Ampoules 60, for example, could be made of any one of a number of materials or combinations of materials such as but not limited to coatings, glasses, plastic materials, metallic materials, gels, ceramics or any combination thereof. Also by way of example, plastic materials could include butyrate or polyethylene rubber, silicone or plastic material, such as, for example, polyvinyl chloride, polyethylene, polyurethane, natural or nitril rubber, or any combination thereof. Other materials, such as a pierceable metal as aluminum or gold may be used for the ampoule 60. Additionally, ampoules 60 can have two or more chambers within, each chamber containing the same or a different fluid 50. Alternately, by way of example, two or more ampoules can be stacked up within a surgical device with each ampoule containing the same or a different fluid 50. An example of a suitable ampoule that can be used is disclosed in U.S. Pat. No. 5,928,611, the entire disclosure of which is hereby incorporated herein by reference.

Adhesive

Adhesive 51 is a fluid 50 contained within an ampoule 60. Adhesive 51 is used to attach bandage 50 to tissue and can be a single or multiple part adhesive. By way of example, adhesive 51 could be a polymerizable and/or cross-linkable material such as but is not limited to a cyanoacrylate adhesive. Alternately the adhesive 51, for example, may be but not limited to a monomeric (including prepolymeric) adhesive composition, a polymeric adhesive composition, or any other natural or artificial compound that can adhere to tissue. In embodiments, the monomer may be a 1,1-disubstituted ethylene monomer, e.g., an .alpha.-cyanoacrylate. When cross linked, the cyanoacrylate changes from a liquid to a solid. A set or cross linked adhesive 51a can be a rigid or flexible and can be non-permeable or permeable. If desired, adhesive 51 can be a single part or dual part adhesive for example an epoxy, or a urethane, or a cyanoacrylate, and/or can contain one or more additives 52. Each part of a two part adhesive can be contained in a chamber in a multi chambered ampoule or in two separate ampoules. Alternately by way of example, ampoule 60 can contain fluids 50 other than an adhesive 51.

Additives

Examples of suitable additives 52 for fluids 50 include, but are not limited to: image enhancing agents, necrosing agents, sclerosing agents, coagulants, ablative agents, therapeutic agents, drugs, medicaments, analeptic agents, anesthesia agents, antidiuretic agents, analgesic agents, antiseptic agents, antispasmodic agents, cardiac agents, depressant agents, diuretic agents, hemostatic agents, hormonal agents, sedative agents, stimulant agents, vascular agents, time release agents, absorbable materials (see above), colorants, plasticizing agents, bulking agents, tamponade materials, thixotropic agents, antibacterial agents, buffers, catalysts, fillers, micro particles, thickeners, solvents, drugs, medicaments, natural or synthetic rubbers, stabilizers, pH modifiers, bioactive agents, cross-linking agents, chain transfer agents, fibrous reinforcements, colorants, preservatives, formaldehyde reducing or scavenging agents, flavorants, perfumes.

Adhesive Initiators

Adhesive initiators 53 are chemical compounds that can rapidly set up or harden an adhesive 51. Adhesive initiators for example can be a fluid 50, a dry compound such as a powder, a coating, or any other form and can induce catalyzation or polymerization in an adhesive 51 by contact with a coating or mixed with the adhesive in some manner. For example, mixing could occur when frangible ampoules 60 for surgical device 25 are constructed with one chamber containing a fluid adhesive 51, and a second chamber containing a fluid adhesive initiator 53. When the ampoule 60 is broken or penetrated, the adhesive 51 and adhesive initiator 53 can mix, saturate the bandage 40, and rapidly set or adhere the saturated bandage 40 to tissue. Alternately by way of example, adhesive initiators could be impregnated within the bandage and initiate setting when saturated with adhesive.

Adhesive initiators 53 can cause polymerization and/or cross-linking of an adhesive such as but not limited to a polymerizable monomer. As used herein, a polymerization initiator is any material that causes a monomer composition applied to a substantially dry tissue (i.e., substantially in the absence of plasma or like tissue fluids) to polymerize in less than 300 seconds at ambient temperature, for example, at approximately 21-25 degrees C. Preferably, the initiator causes the monomer composition to polymerize in less than 150 seconds at ambient temperature, more preferably within 60 seconds to 120 seconds. As used herein, a polymerization rate modifier is any material that changes the rate at which a polymerizable monomer would polymerize in the absence of that material. Preferably, the rate modifier accelerates the rate of the polymerization reaction, although for particularly fast-acting monomers it may decelerate that rate.

Particular adhesive initiators 53 for particular monomers may be readily selected by one of skill in the art without undue experimentation. Control of the molecular weight distribution of the applied adhesive can be enhanced by selection of the concentration and functionality of the initiator or accelerator vis-a-vis the selected monomer. Suitable polymerization initiators and accelerators for cyanoacrylate compositions include, but are not limited to, detergent compositions; surfactants, including nonionic surfactants such as polysorbate 20 (e.g., Tween 20™; ICI Americas), polysorbate 80 (e.g., Tween 80™; ICI Americas), and poloxamers; cationic surfactants such as tetrabutylammonium bromide; anionic surfactants, including quaternary ammonium halides such as benzalkonium chloride or its pure components, and benzethonium chloride; stannous octoate (tin(II)2-ethylhexanoate), and sodium tetradecyl sulfate; and amphoteric or zwitterionic surfactants such as dodecyldimethyl(3-sulfopropyl)ammonium hydroxide, inner salt; amines, imines, and amides, such as imidazole, tryptamine, urea, arginine and povidine; phosphines, phosphites and phosphonium salts, such as triphenylphosphine and triethyl phosphite; alcohols such as ethylene glycol; methyl gallate; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat™ 336 (General Mills, Inc., Minneapolis, Minn.); organometallics; manganese acetylacetonate; radical initiators and radicals, such as di-t-butyl peroxide and azobisisobutyronitrile; and bioactive compounds or agents.

Alternately, the adhesive initiator 53 may be a bioactive material, including quaternary ammonium halides such as alkylbenzyldimethylammonium chloride (benzalkonium chloride; BAC) its pure components, or mixtures thereof, especially those with an alkyl containing 6-18 carbon atoms; benzethonium chloride; and salts of sulfadiazine. Cobalt napthenate can be used as an accelerator for peroxide. Other suitable bioactive materials are disclosed in U.S. Pat. No. 5,928,611 to Leung and U.S. patent application Ser. No. 08/920,876, filed Aug. 29, 1997, Ser. No. 09/430,176 filed Oct. 29, 1999, and Ser. No. 09/430,177, filed Oct. 29, 1999, the entire disclosures of which are incorporated herein by reference.

Other examples of adhesives 51, additives 52, and adhesive initiators 53, may be found in United States Application 20040190975 by Goodman et al. which is herein incorporated by reference in its entirety.

Additionally, the adhesive 51 may be polymerized or cured or set by exposure such as but not limited to light, any external frequency exposure, vibration, pressure waves, and heat.

Surgical Device with Push Actuator

Figure 4:
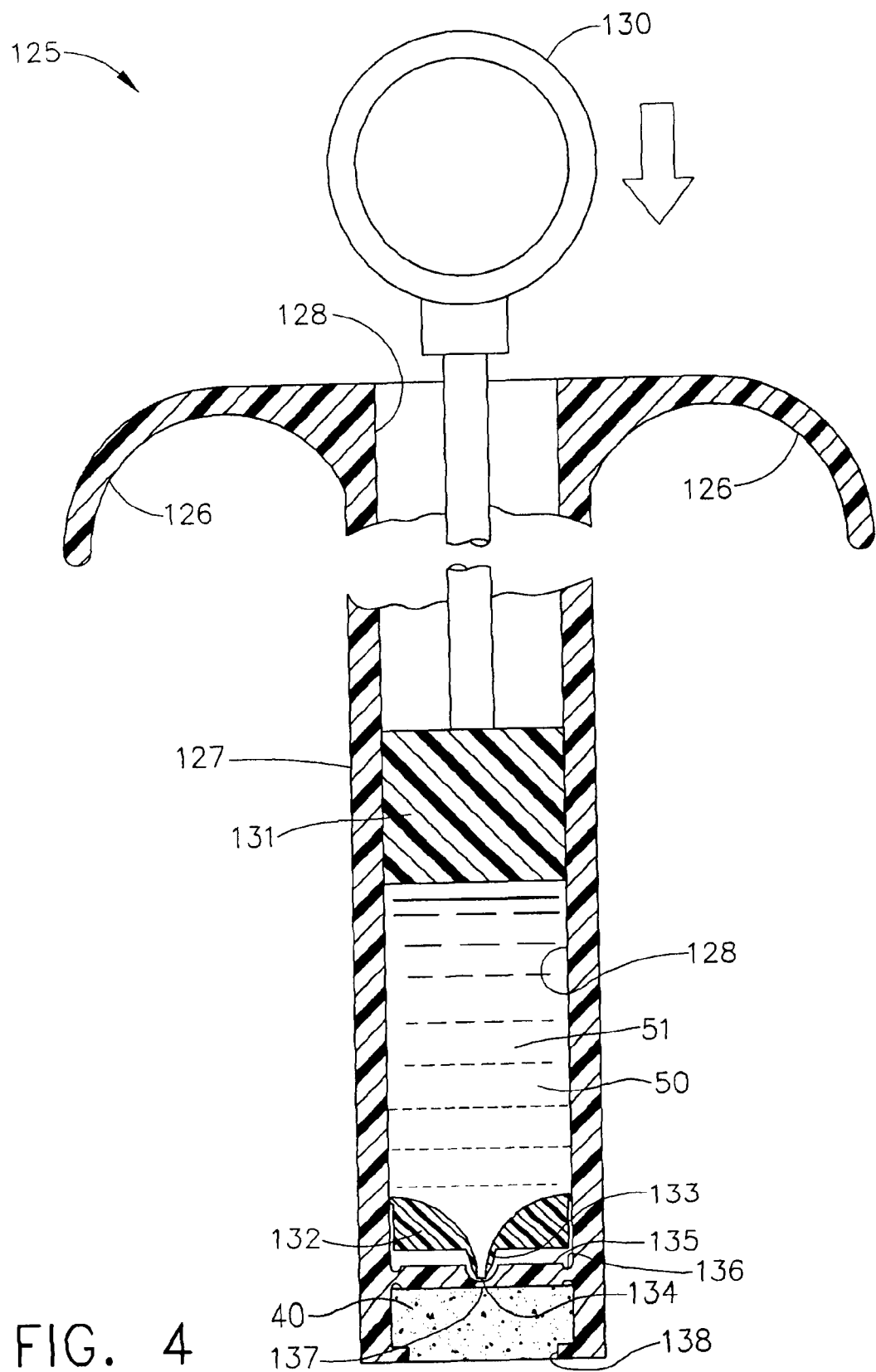
FIG. 4 is a cross sectional view of an alternate embodiment of a surgical device that can adhere the porous disk bandage onto tissue with a push actuation.
Figure 5:
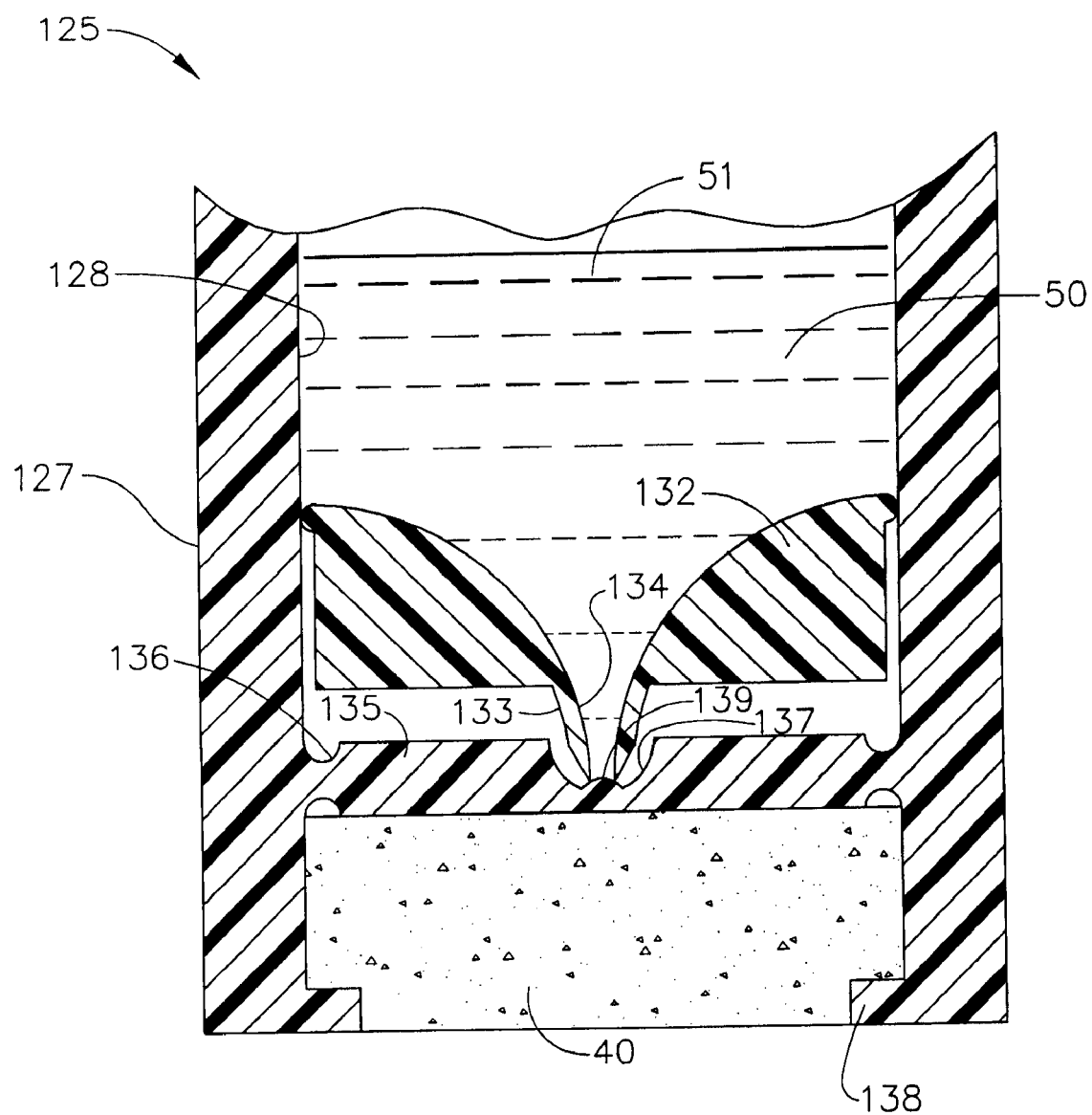
FIG. 5 is a partial cross sectional view of a distal end of the alternate surgical device.

FIGS. 4 and 5 show an alternate push surgical device 125 having a rigid frame 127 with grips 126 extending from a proximal end therefrom. A push actuator 130 slidably mounts within a proximal end of a bore 128 within rigid frame 127 and is longitudinally moveable therein by pushing or pulling. A distal end of push actuator 130 has a piston 131 that seals with and is slidably movable within bore 128. A fluid 50 is located within bore 128, proximal to piston 131 and distal to a needle piston 132. For this example, fluid 50 is an adhesive 51. The figure shows an excessive volume of fluid 50 for illustration sake but the intent is to provide a quantity of fluid 50 sufficient to fill the bandage 40. Needle piston 132 is slidably moveable within bore 128, has a sharp 133 on the distal end, and an opening 134 extending longitudinally therethrough. Sharp 133 is in contact with a pierce area 137 of a pierceable bandage backer, or barrier 135 (FIG). Barrier 135 seals a distal end of bore 128 of frame 127 and seals needle piston opening 134 with a thin pierce area 137 of barrier 135 to prevent egress of fluid 50 therefrom. Alternately, as shown in FIG. 5, a small plug 139 can be provided to plug the needle piston opening 134. Barrier 135 also has a thin shear area 136 about the periphery. Shear area 136 is shown by way of example as a thin ring about the circumference, but could be a plurality of radial grooves. As shown, by way of example, frame 127 and barrier 135 can be molded from an engineering thermoplastic as one piece. Suitable engineering thermoplastic materials can include but are not limited to polyethelene, polypropelene, styrene, vectra and the like. Bandage 40 is held in place in frame 127 by a stop ring 138. Stop ring 138 can also stop barrier 135 from being ejected from frame 127 after shearing.

During surgery, the surgical device 125 can be held in a surgeons hand by placing his thumb in actuator 130 and the first two fingers of the same hand under grips 126. Pushing distally on actuator 130 moves piston 131 distally to push on incompressible fluid 50. Fluid 50 hydraulically transmits the compression force to needle piston 132. Needle piston 132 pushes sharp 133 into pierce area 137 of barrier 135 to pierce therethrough. Once sharp 133 has pierced pierce area 137, fluid 50 (adhesive 51) can flow from opening 134 extending through needle piston 132 and saturate bandage 40. Continued depression of actuator 130 dispenses some or all of fluid 50 into bandage 40 and brings piston 131 into contact with needle piston 132. Continued pressure forces needle piston 132 into hard contact with barrier 135 and breaks, deforms, and/or shears shear area 136. Once shear area 136 is sheared, continued pressure on actuator 130 pushes piston 131, needle piston 132, barrier 135, and fluid 50 saturated bandage 51 distally to release bandage 40 from stop ring 138 and surgical device 125 and into place on tissue. Surgical device 125, sans bandage 40 and adhesive 51 can now be removed. If desired, barrier 135 can be ejected along with bandage 50 and adhesive 51, or can be constrained by stop ring 138.

Whereas a breakable barrier 135 is described above, barrier 135 is not limited to that particular embodiment. By way of example, the barrier 135 could be a part of the frame 127, a thin foil or plastic seal like found on commercially available drug and food products, a separate component captured by the frame 127, or a section of the bandage 40. Additionally, surgical device 125 can be any length and can be used for open, laparoscopic, and endoscopic applications.

Surgical Device with Rotary Actuator and Multiple Bandages

Figure 6:
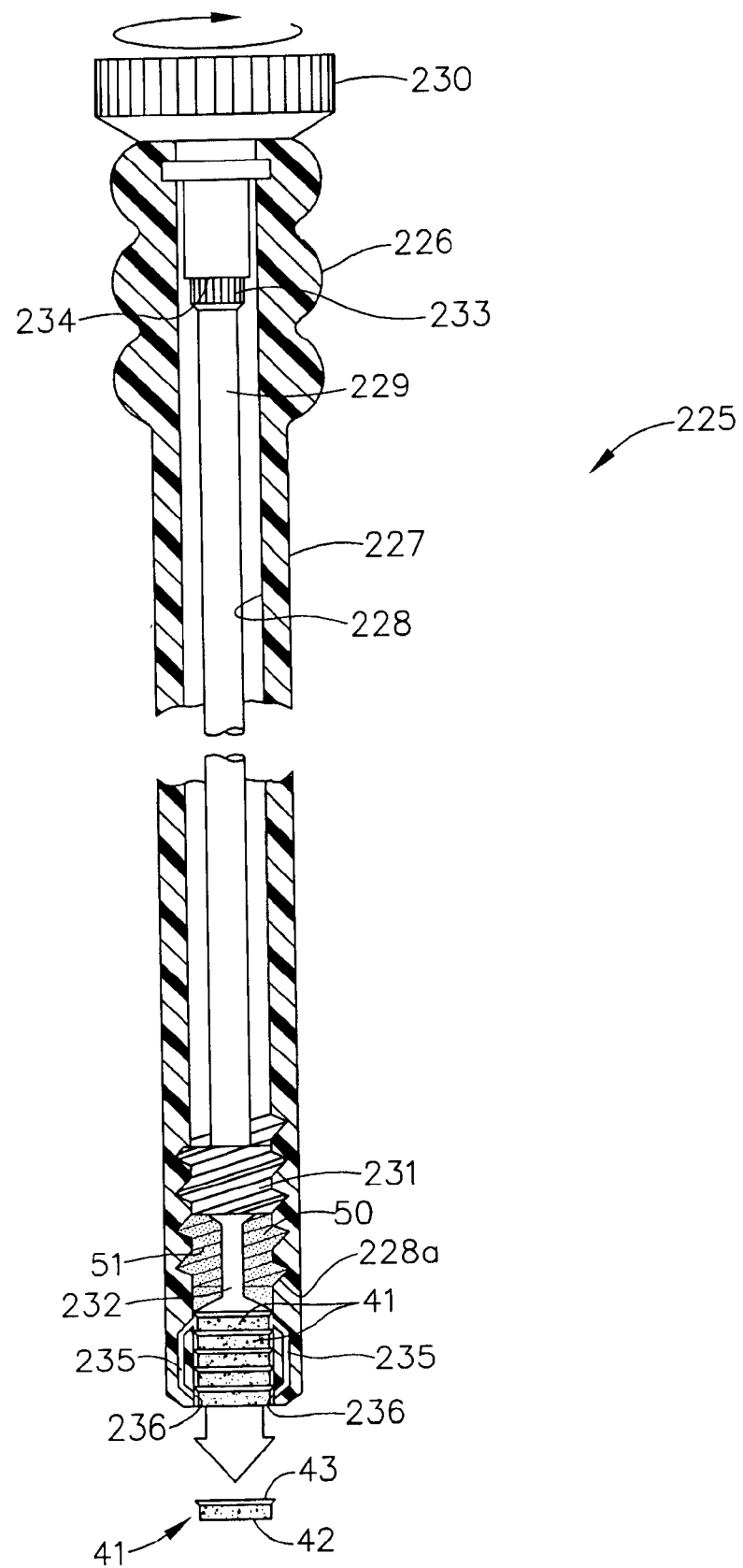
FIG. 6 is a cross sectional view of an alternate embodiment of a surgical device that has a surgical bandage with a non-permeable barrier layer and one or more porous layers, the surgical device releasing the adhesive into a distal most bandage and releasing the bandage in response to a rotary actuation.

FIG. 6 shows another alternate embodiment of a surgical device 225 having a rotary actuator 230 and containing a plurality of alternate bandages 41 at a distal end of a bore 228 extending within frame 227. Alternate bandages 41 have a proximal barrier 43 and a disk shaped porous pad 42. Barrier 43 is non-permeable and/or impervious to fluids, and forms a sliding seal with the bore 228. Porous pad 42 can be identical to bandage 40 and can be constructed from one or more layers and from any materials listed above. Rotation of rotary actuator 230 ejects alternate bandage 41 saturated in a fluid 50, and for this example, fluid 50 is an adhesive 51 such as a cyanoacrylate. Surgical device 225 can be made in any length which makes it well suited for open surgery or endoscopic use where it can be inserted into a trocar and into a patient and has a handle 226 to grasp.

Rotation of rotary actuator 230 rotates a shaft 229 which rotates a threaded first piston 231 in a threaded portion 228a of a bore 228 extending through a housing 227. A plunger 232 extends distally from threaded piston 231 and, as threaded piston 231 rotates, the threaded piston 231 and plunger 232 move in a distal direction. Plunger 232 is in contact with the proximal most bandage 41 of a plurality of or stack of bandages 41, and pushes the stack of bandages 41 distally to eject them one at a time from surgical instrument 22'. Shaft 229 both rotates and moves distally and has a toothed connector 233 at a proximal end that slidably mounts and engages with a toothed connector socket 234 in rotary actuator 230. As threaded piston 231 rotates and moves distally, toothed connector 233 slides distally in toothed connector socket 234 and the teeth remain operably engaged with rotary actuator 230.

Fluid 50 is located in bore 228 distally to threaded piston 231. Distal movement of threaded piston 231 moves fluid 50 distally, around plunger 232 and into a first opening 237 of at least one passageway 235. Passageways 235 pass through frame 227 around the stack of bandages 41 and have at least one second opening or distal orifice 236 adjacent to the sides of the distal most bandage 51 in the stack of bandages 51. Thus, rotation of activator 230 moves the stack of bandages 41 distally past first opening 237, pushes fluid 50 into passageways 235, saturates the distal most one of bandages 41 with fluid 50 (adhesive 51) from distal orifice 236 and advances and releases the saturated distal most bandage 41 onto tissue. Continued rotations of rotary actuator 230 saturate and release the additional bandages 41 one at a time from the surgical device 225 until all are dispensed.

Barrier 43 of bandage 41 creates a seal with bore 228 to prevent fluid 50 from migrating into un-saturated bandages 51 proximal to the distal most saturated bandage. Barrier 43 of the proximal most bandage also creates a seal with bore 228 to prevent the passage of fluid 50 therethrough.

Alternate Surgical Device with Rotary Actuator and Multiple Bandages

Figure 7:
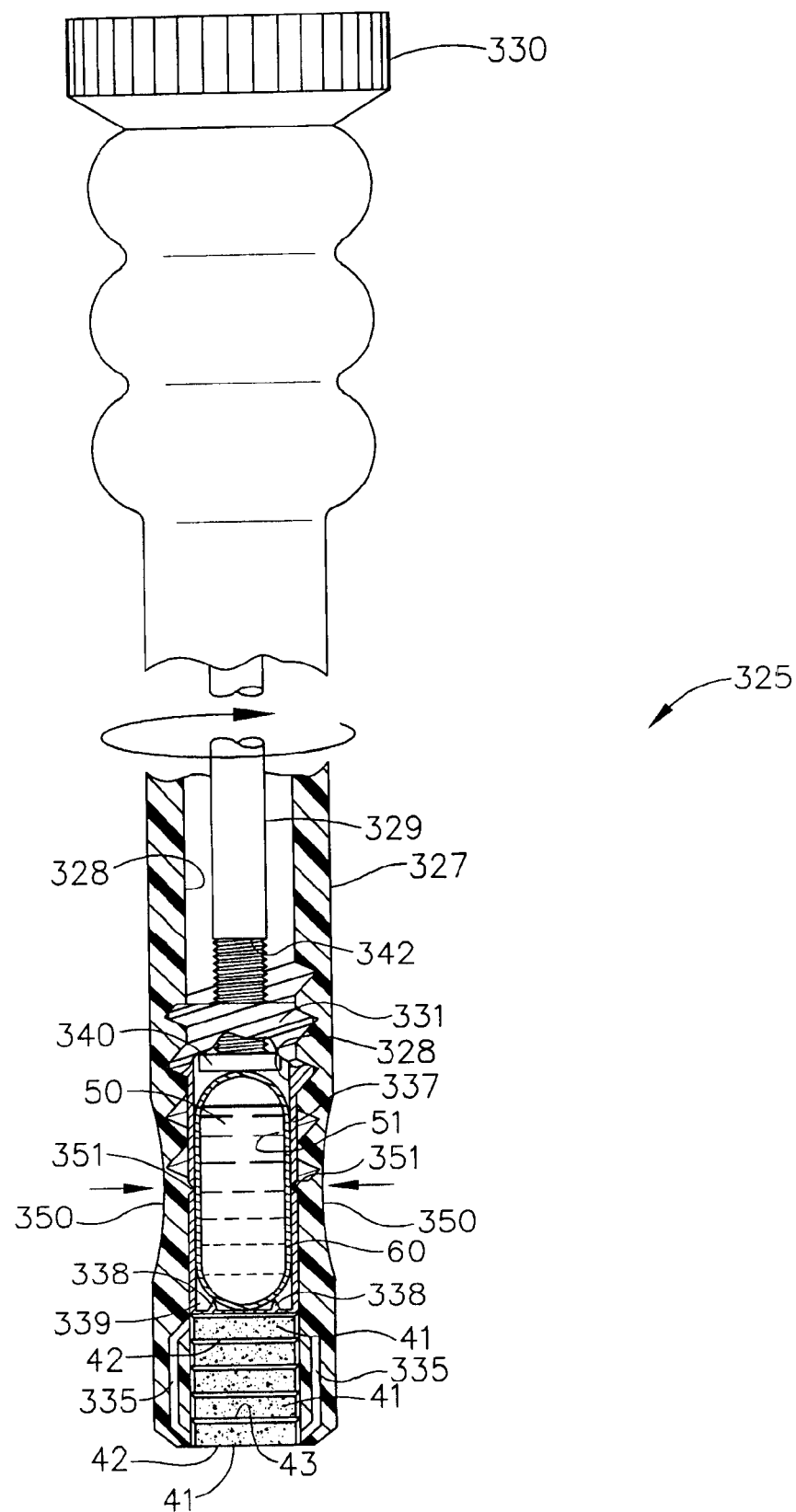
FIG. 7 is a cross sectional view of an alternate embodiment of the surgical device of claim 6 wherein the adhesive is stored in a frangible ampoule breachable by a squeezing actuation, and the bandage and adhesive are released from the surgical device by rotary motion.

FIG. 7 shows an alternate example of the surgical device 225 of FIG. 6. The alternate example surgical device 325 has a rotary actuator 330 and contains a frangible ampoule 60 containing a fluid 50 such as an adhesive 51. Unlike the surgical device 225, the adhesive 51 is stored within a frangible ampoule 60 and requires breakage of the frangible ampoule 60 to release the adhesive into a bore 328 of the frame 327. One or more alternate bandages 41 are located in a proximal portion of bore 328 and have barrier 43 and porous pad 42. Each of the barriers 43 forms a sliding seal with bore 328. Rotation of the rotary actuator moves the adhesive 51 and one or more alternate bandages 41 distally, releases the adhesive 51 to saturate a distal most one of the one or more alternate bandages 41 and applies the saturated alternate bandage onto tissue.

A first piston 331 is threadably engaged with and resides within bore 328 of frame 327, and is operably attached to the rotary actuator 330. A hollow pusher tube 337 extends distally from first piston 331 to contact the non-permeable barrier 43 of the proximal most one of the one or more bandages 41, and contains ampoule 60 and adhesive 51 within a hollow 339 therein. The hollow pusher tube 337 is deformable by a squeeze load (see arrows), returns to a tubular shape when the squeeze load is removed, and hollow 339 has a volume greater than ampoule 60. A plurality of "V" shaped fluid ports 338 are located about a distal end of pusher tube 337 and fluidly connect hollow 339 with the bore 328. The frame 327 has a deflectable portion 350 or squeeze actuators about the hollow pusher tube 337 and one or more stress concentrators 351 extending therein. Squeezing of the deflectable portion 350 moves stress concentrators 351 inward to deflect hollow pusher tube 337 inwardly and breach ampoule 60 to release adhesive 51 into hollow 339 and bore 328.

A second piston 340 is located within hollow 339 of the hollow pusher tube 337 and is threadably attached to first piston 331 such that with ampoule 60 breached, rotation of the rotary actuator 330 a first amount moves the second piston 340 distally within the stationary hollow pusher tube 337. Since the volume of hollow 339 is greater than ampoule 60, a very small gap is provided between second piston 340 and hollow 339 for air passage yet prevent passage of viscous adhesive 51 therethrough. This gap allows second piston 340 to move distally the first amount to push down the remains of the breached ampoule 60, to separate the air from the fluid 50 or adhesive 51 within hollow 339, and to drive the adhesive 51 from the hollow 339, through openings 338 and into the bore 328 of the frame 327. A small gap exists between the bore 328 and the hollow pusher tube 337 so that fluid 50, 51 can flow out of openings 338 and into the gap (not shown).

Rotation of the actuator 330 a second amount brings shoulder 342 of shaft 329 into engagement with first piston 331 and operably locks the second piston 340 to the first piston 331 so that further rotation of the rotary actuator 331 rotates and moves the first piston 331 to move the adhesive 51 and one or more bandages 41 distally to release the seal or barrier 43 by opening passageways 335 to fluid passage (as described above with like passageways 225), to saturate the distal most bandage 41, and release the saturated distal most bandage 41 onto tissue.

Thus, squeezing of the deflectable portion 350 of frame 327 releases the adhesive 51 from the ampoule and rotation of rotary actuator 330 releases the adhesive seal, saturates the distalmost bandage and ejects alternate bandage 41 saturated in adhesive onto tissue. Continued small rotations of rotary actuator 330 saturate and release the additional bandages 41 one at a time from the surgical device 325 until all are dispensed. Surgical device 325 can be made in any length which makes it well suited for open surgery or endoscopic use where it can be inserted into a trocar and into a patient.

Additionally, by way of example, surgical devices 25, 125, 225 and 325 may contain media that requires one or more parts. If two parts, at least one part must be a fluid or fluid carrier of the desired media.

And, by way of example, mixing of fluids 50, if required, may be manual or mechanical. Mechanical mixing may utilize mixers such as spiral mixers used with two part adhesive systems and two part casting compounds and the like. Mixing of the fluid 50 may cause a reaction to create the desired properties. For example, an adhesive 51 and an adhesion initiator 52 can be mixed to cause a polymerization reaction to begin the polymerization or "setting" of the adhesive to speed up the adhesion process.

Additionally, surgical devices 25, 125, 225 and 325 may be syringe based or captured into a housing in any form of hand orientation such as pistol grip. Alternative activation means by levers, finger trigger, and thumb push are conceived as well as power, mechanical assist, pneumatics, hydraulics and the like. Surgical devices 25, 125, 225 and 325 may be single shot, multi-shot, a reloadable single patient device or a reloadable reusable device that can accommodate fluid 50 and/or bandage 40, 41 reloads. Devices shown are axially dispensing devices but, by way of example, can be articulated or oriented to a variety of positions.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, wherein a plastic breakable barrier having a breakable thin section about the periphery is described above, the device is not limited to that embodiment and any barrier that can seal a fluid within the surgical device and release the fluid would be covered. For example, a valve, a membrane, a dissolving seal, a foil seal, opening petals, a plug, a variable sized orifice, an explosive cover, a chemically reactive or meltable seal, and the like would all be embodiments.

Also by way of example, wherein the surgical devices above teach a liquid such as an adhesive, the surgical device is not limited to just that embodiment. For example, the bandage or bandages can have a pre-applied sticky or sticky-note type adhesive material on one side, a central layer of absorbable material and a non-penetratable film on the other side. The fluid contained within the surgical device could be a therapeutic drug needed to elute over time for the treatment of cancer. Activation of the surgical device could soak the bandage in the therapeutic drug and eject the bandage onto tissue, where the pre-applied adhesive would adhere to tissue. The barrier material could be such that the pre-applied sticky adhesive could be easily separated therefrom enabling multiple bandages to be placed.

Also by way of example, the surgical devices described above are not limited to the ampoule or fluids placed thereon. Surgical device could be disssasemblable or refillable and fluids may be placed within surgical device at any time.

And, by way of example, multiple bandage dispensing mechanisms such as those described above can be used with squeeze actuators, rotating actuators, push actuators or any other bandage dispensing mechanism.

What is claimed is:

1. A surgical device for applying a bandage to tissue, the surgical device comprising:
   a) a frame having a proximal end and a distal end, the frame comprising a deflectable wall and at least one rib, wherein the deflectable wall defines at least one chamber, and wherein the at least one rib extends along the deflectable wall and about at least a portion of the proximal end of the frame;
   b) an adhesive dispensably sealed within the at least one chamber of the frame;
   c) a bandage having at least one porous layer, the bandage located at the proximal end of the frame and adjacent to the adhesive dispensably sealed within the at least one chamber; and
   d) an actuation mechanism comprising at least one actuator, wherein the at least one actuator is mounted to the at least one rib of the frame and is operably coupled to the adhesive and the bandage, and wherein actuation of the actuation mechanism dispenses the adhesive to saturate the at least one porous layer of the bandage, and releases the saturated bandage from the surgical device onto tissue.

2. The surgical implant of claim 1 wherein the adhesive is one or more compounds selected from the group consisting of a polymerizable monomer, a polymerizable 1,1,1,1-disubstituted ethylene monomer, a cyanoacrylate formulation, and an additive.

3. The surgical device of claim 2 wherein the bandage further comprises one or more compounds selected from the group consisting of an additive, an adhesive, and an adhesive initiator.

4. The surgical device of claim 3 wherein the frame is squeezably deformable.

5. The surgical device of claim 4 wherein the adhesive is dispensably sealed within a frangible ampoule located within the at least one chamber of the squeezably deformable frame.

6. The surgical device of claim 5 wherein the actuation mechanism includes at least one stress concentrator, wherein when the actuation mechanism is squeezed to deform the squeezably deformable frame, the at least one stress concentrator contacts and breaches the frangible ampoule to dispense the adhesive therefrom.

7. The surgical device of claim 6 wherein the actuation mechanism includes one or more clamps releasably holding the bandage to the surgical device, wherein when the actuator mechanism is squeezed, the one or more clamps release the bandage from the surgical device.

8. The surgical device of claim 3 wherein the adhesive is dispensably sealed within the at least one chamber by a breachable seal, wherein the breachable seal is one or more selected from the group consisting of:
   a) a penetratable film;
   b) a penetratable foil;
   c) a reduced thickness piercing area;
   d) a frangible barrier having one or more breakable radial grooves about the barrier, and
   e) a frangible barrier having a breakable groove about a periphery of the frangible barrier, 9. The surgical device of claim 6, further comprising an opening, the opening extending through the deflectable wall of the frame.

10. The surgical device of claim 9, wherein the actuation mechanism is pivotally attached to the frame by positioning the at least one stress concentrator within the opening in the deflectable wall.

11. The surgical device of claim 1, wherein the frame comprises one or more squeezably deformable materials selected from the group consisting of a polyethylene, polypropylene, nylon, and aluminum.

12. The surgical device of claim 1, wherein the device further comprises a plug that is fixedly attached to the distal end of the frame.

13. The surgical device of claim 1, wherein the frame defines a longitudinal axis, the at least one rib extending substantially perpendicular to the longitudinal axis.

14. The surgical device of claim 1, wherein the frame further comprises a plurality of notches at the proximal end of the frame, the notches being operably configured to receive the bandage.

15. The surgical device of claim 1, wherein the distal proximal end of the frame further comprises a passage through which the adhesive flows after the actuation mechanism is actuated.

* * * * *